(12) United States Patent
Mikolajczak et al.

(10) Patent No.: US 10,763,920 B2
(45) Date of Patent: Sep. 1, 2020

(54) MULTIPOLYMER SENSOR ARRAY UTILIZING NFC

(71) Applicant: Infineon Technologies AG, Neubiberg (DE)

(72) Inventors: Adrian Mikolajczak, Los Altos, CA (US); Marc Haylock, San Jose, CA (US); Christopher Woodthorpe, Los Gatos, CA (US); Joerg Poeltl, Gratwein-Strassengel (AT)

(73) Assignee: INFINEON TECHNOLOGIES AG, Neubiberg (DE)

( * ) Notice: Subject to any disclaimer, the term of this patent is extended or adjusted under 35 U.S.C. 154(b) by 225 days.

(21) Appl. No.: 15/987,145

(22) Filed: May 23, 2018

(65) Prior Publication Data
US 2019/0363757 A1    Nov. 28, 2019

(51) Int. Cl.
*H02J 7/02*    (2016.01)
*H04B 5/00*    (2006.01)
(Continued)

(52) U.S. Cl.
CPC ............ *H04B 5/0037* (2013.01); *H02J 7/025* (2013.01); *H02J 50/05* (2016.02); *H02J 50/12* (2016.02); *H04B 5/0031* (2013.01)

(58) Field of Classification Search
USPC ....................................................... 320/108
See application file for complete search history.

(56) References Cited

U.S. PATENT DOCUMENTS

| 9,967,001 B2 | 5/2018 | Biederman |
| 2013/0338769 A1* | 12/2013 | Boyden ............... A61F 2/12 623/8 |

(Continued)

FOREIGN PATENT DOCUMENTS

| CN | 107432738 A | 12/2017 |
| WO | 2014158405 A2 | 10/2014 |
| WO | 2017218947 | 12/2017 |

OTHER PUBLICATIONS

Dehennis, A., "An NFC-Enabled CMOS IC for a Wireless Fully Implantable Glucose Sensor," IEEE Journal of Biomedical and health Informatics, Jan. 2016, pp. 18-28, vol. 20, No. 1, IEEE, Piscataway, NJ.

(Continued)

*Primary Examiner* — Robert Grant
(74) *Attorney, Agent, or Firm* — Slater Matsil, LLP (57) ABSTRACT

A sensor device includes a first detector circuit, a near field communication (NFC) circuit, and a sensor package. The first detector circuit configured to detect a stimulus using a resistive change polymer type detector, a capacitive shift polymer type detector, a dielectric change polymer type detector, a graphene based sensor, or a metal-oxide (MOX) type detector. The NFC circuit having an NFC powered receiver and an NFC data transceiver. The NFC power receiver configured to receive power from a mobile device using an NFC standard protocol and to provide operating power for the sensor device. The NFC data transceiver configured to transmit data to the mobile device using the NFC standard protocol, the data corresponding to the first stimulus. The sensor package configured to house the first detector circuit and the NFC circuit.

29 Claims, 6 Drawing Sheets

(51) Int. Cl.
    *H02J 50/05*    (2016.01)
    *H02J 50/12*    (2016.01)

(56)  References Cited

U.S. PATENT DOCUMENTS

2015/0351648 A1\* 12/2015 Harvey .................. A61B 5/686
                                                             600/561
2016/0066894 A1    3/2016 Barton-Sweeney

OTHER PUBLICATIONS

Escobedo, P., "Flexible Passive near Field Communication Tag for Multigas Sensing," Analytical Chemistry, Jan. 10, 2017, pp. 1697-1703, vol. 89, No. 3, ACS Publications.
Lazaro, A., "A Survey of NFC Sensors Based on Energy Harvesting for IoT Applications," Sensors, Nov. 2, 2018, 26 pages, vol. 18, No. 11, MDPI.
Wan An, B., "Smart Sensor Systems for Wearable Electronic Devices," Polymers, Jul. 25, 2017, 40 pages, vol. 9, No. 12, MDPI.
Xu, G., "Passive and wireless near field communication tag sensors for biochemical sensing with smartphone," Sensors and Actuators B: Chemical, Feb. 27, 2017, pp. 748-755, vol. 246, Elsevier BV.
Alminde, O., "New Integrated NFC Tag/Sensor Devices: How Low-Cost, Low-Power RF Technology Enables New Applications", Technical Article, Feb. 19, 2015, 7 pages.
Boden, Rian, https://www.nfcworld.com/2014/04/10/328699/ingenic-unveils-developer-board-wearable-devices-nfc/, "Ingenic unveils developer board for wearable devices with NFC", Apr. 10, 2014, 5 pages.
Sense, https://www.melexis.com/en/products/sense, Melexis Inspired Engineering, May 2018, 10 pages.

\* cited by examiner

MULTIPOLYMER SENSOR ARRAY UTILIZING NFC

TECHNICAL FIELD

The present invention relates generally to an electronic device, and, in particular embodiments, to a system and method for a sensor having a near field communication (NFC) circuit.

BACKGROUND

An electronic sensor is a device that measures a physical or chemical stimulus such as gas, pressure, heat, light, moisture, presence of a particulate, or a specific health parameter of an individual and converts the measurement into a digital or an analog signal. Typically, the electronic sensor is made of a sensor module and an electronic circuit. The sensor module senses environmental information and the electronic circuit converts the environmental information to a signal.

A characteristic feature of the typical health and gas sensor is a limited operating life, limited operating duration, frequent calibration requirement, and a limited targeted audience. As a result, mobile device suppliers have been hesitant to directly integrate these types of sensors into a mobile device, which typically outlast the operating life of the sensors, and may only be useful for a subset of consumers.

SUMMARY

In accordance with an embodiment, a sensor device includes a first detector circuit, a near field communication (NFC) circuit, and a sensor package. The first detector circuit configured to detect a stimulus using a resistive change polymer type detector, a capacitive shift polymer type detector, a dielectric change polymer type detector, a graphene based sensor, or a metal-oxide (MOX) type detector. The NFC circuit having an NFC powered receiver and an NFC data transceiver. The NFC power receiver configured to receive power from a mobile device using an NFC standard protocol and to provide operating power for the sensor device. The NFC data transceiver configured to transmit data to the mobile device using the NFC standard protocol, the data corresponding to the first stimulus. The sensor package configured to house the first detector circuit and the NFC circuit.

In accordance with another embodiment, a method for sensing a stimulus using a sensor device includes receiving, by a near field communication (NFC) circuit of the sensor device, an induced current from a mobile device using an NFC standard protocol, the induced current being used to power the sensor device. The method further includes detecting, by a detector circuit of the sensor device, a stimulus. The detector circuit being a resistive change polymer, a capacitive shift polymer, a dielectric change polymer, a graphene based sensor, or a metal-oxide (MOX) type detector. The method also includes converting, by a sensor circuit of the sensor device, the stimulus to a digital signal and transmitting, by an NFC data transceiver of the sensor device, the digital signal to the mobile device using the NFC standard protocol.

In accordance with yet another embodiment, a sensor device includes a detector circuit, a near field communication (NFC) circuit, a sensor circuit, a non-transitory memory storage, and a processor. The detector circuit includes a resistive change polymer, a capacitive shift polymer, a dielectric change polymer, a graphene based sensor, or a metal-oxide (MOX) type detector. The NFC power receiver includes an antenna and a power management unit. The NFC circuit configured to receive an induced current from a mobile device using an NFC standard protocol, where the induced current is used to operate the sensor device. The non-transitory memory storage includes instructions and the processor is in communication with the non-transitory memory storage. The processor executes instructions to detect a stimulus using the detector circuit, convert the stimulus to a digital signal using the sensor circuit, and transmit the digital signal to the mobile device using the NFC standard protocol by the NFC data transceiver circuit.

BRIEF DESCRIPTION OF THE DRAWINGS

For a more complete understanding of the present invention, and the advantages thereof, reference is now made to the following descriptions taken in conjunction with the accompanying drawings, in which.

DETAILED DESCRIPTION OF ILLUSTRATIVE EMBODIMENTS

The structure, manufacture, and use of embodiments are discussed in detail below. It should be appreciated, however, that this disclosure provides many applicable inventive concepts that can be embodied in a wide variety of specific contexts. The specific embodiments discussed are merely illustrative of specific ways to make and use the invention, and do not limit the scope of the invention.

Features from different embodiments may be combined to form further embodiments unless noted otherwise. Variations or modifications described with respect to one of the embodiments may also be applicable to other embodiments.

A sensor provides a representation of a presence or a level of presence associated with a physical or a chemical quantity or property. An electronic sensor provides a representative electronic signal in the form of, for example, a voltage or a current.

The prevalence of mobile electronics (e.g., phones, smart watches, tablets, etc.) and the diverse list of capabilities within these devices, enable device manufacturers to provide numerous services in a small form factor. The increased processing power and adaptability in functionality, provides an opportunity to embrace a wide variety of sensors in a mobile device ecosystem. Sensors including, for example, pulse sensors, oxygen sensors, temperature sensors, blood pressure sensors, airflow sensors, electrocardiogram (ECG) sensors, electromyography (EMG) sensors, galvanic skin response (GSR) sensors, glucometer sensors, dehydration sensors, gas sensors, ambient light sensors, and particulate sensors are often incorporated within this ecosystem.

A mobile device may have a sensor as an internal component, for example, using a microelectromechanical (MEMS) sensor within the mobile device package. However, the addition of sensors results in additional mobile device cost, additional power consumption, and a compromise in volumetric space within the mobile device that may be better used to enhance other features of the mobile device with, for example, larger batteries, additional antennas, etc.

Additionally, some sensors, in particular aging sensors, may have a shorter operating life than a consumer mobile device or may be useful to a subset of the consumers of the mobile device. An aging sensor is a type of sensor that is particularly susceptible to a decrease in sensor performance due to aging induced effects, such as exposure to temperature and humidity over time. An example of an aging sensor is a polymer based sensor (e.g., resistive change polymer, capacitive shift polymer, dielectric change polymer, etc.), a graphene based sensor, or a metal-oxide (MOX) sensor. As an example, a sensor may be devised in the form of a polymer based breath analyzer to detect the tuberculosis (TB) bacteria when exposed to the air molecules exhaled by an individual. An implementation of this sensor in, for example, cell phones in high burden TB countries would be welcomed; however, the same implementation may be an unnecessary cost additive in low burden TB countries.

Additionally, limited sensor operating life (6 to 12 months) and periodic sensor calibration may result in the obsolescence of that particular sensor during portions of the mobile device's life. As a result, device manufacturers may have a guarded approach in directly integrating these types of sensors in a mobile device.

It would be advantageous for device manufacturers to provide a modular system, where the sensor is external to the mobile device, yet capable of collecting exchange stimulus measurements. In such a system, the sensor may collect stimulus information and the mobile device may be used to analyze this information. According to various embodiments described herein, and in accordance with the general trends described herein above, a sensor having a near field communication (NFC) circuit is presented that measures stimuli and transfers information to a mobile electronic device using NFC standard technology.

Figure 1:
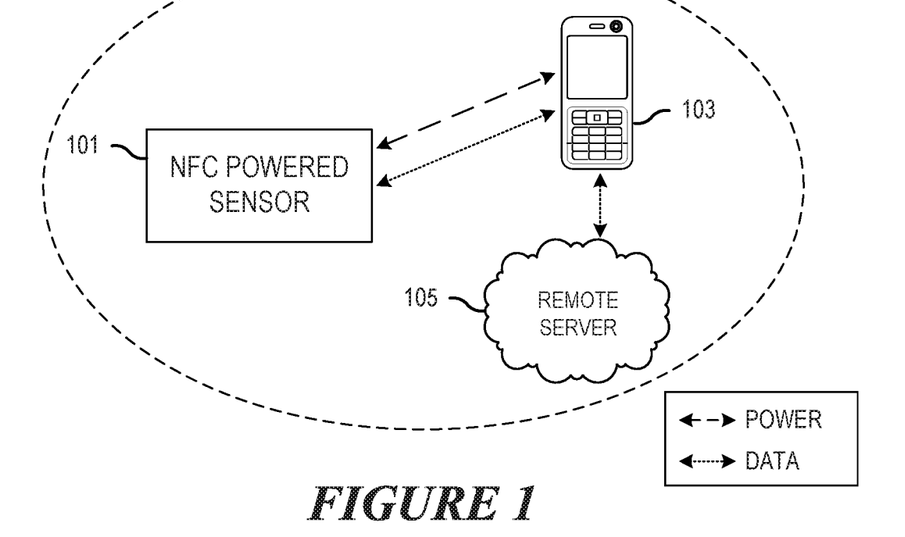
FIG. 1 is a diagram of an embodiment network for communicating power and data.
Figure 2:
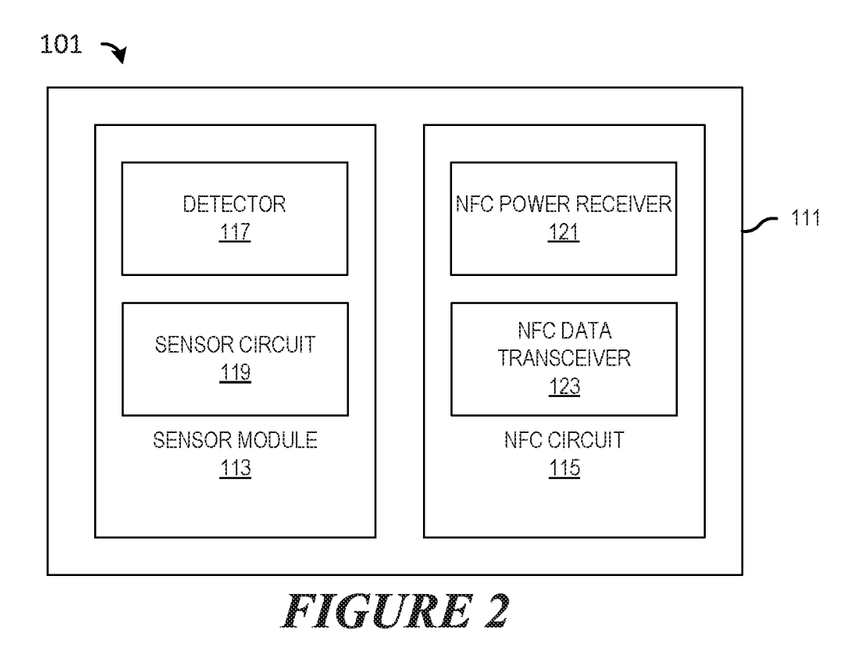
FIG. 2 is a block diagram of an embodiment NFC powered sensor.
Figure 3:
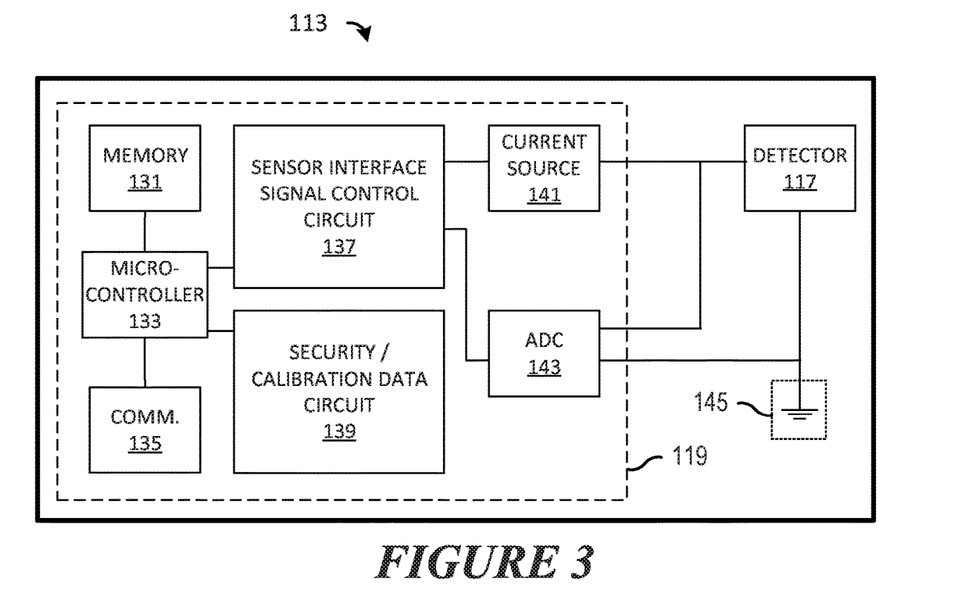
FIG. 3 is a block diagram of an embodiment sensor module.
Figure 4:
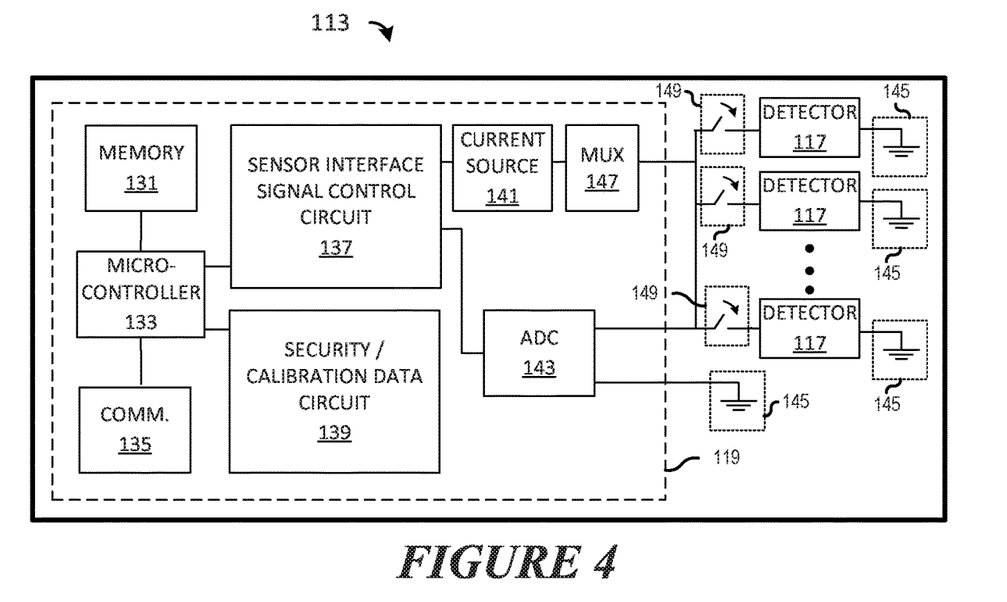
FIG. 4 is a block diagram of another embodiment sensor module.
Figure 6:
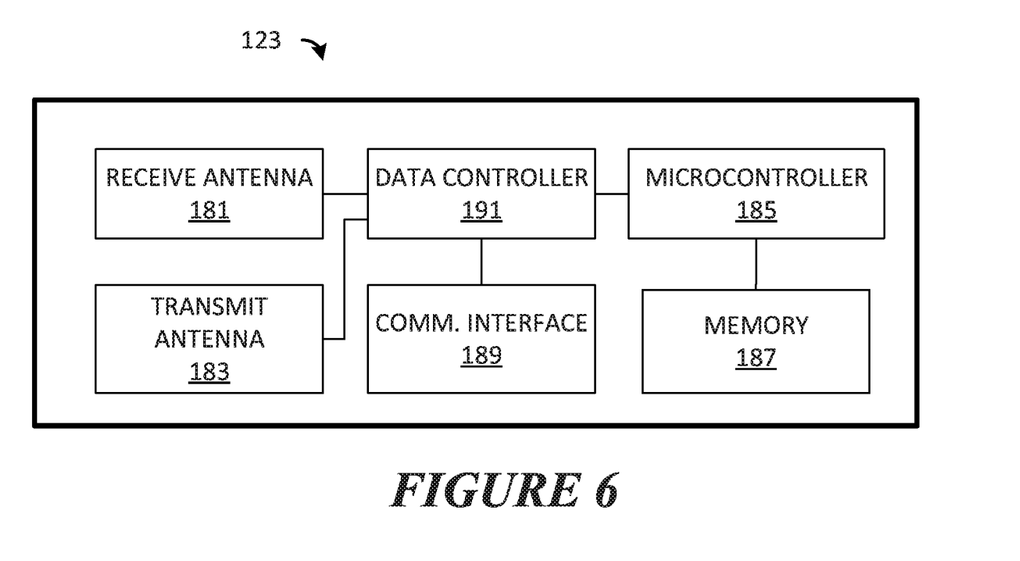
FIG. 6 illustrates a block diagram of an embodiment NFC data transceiver.
Figure 7:
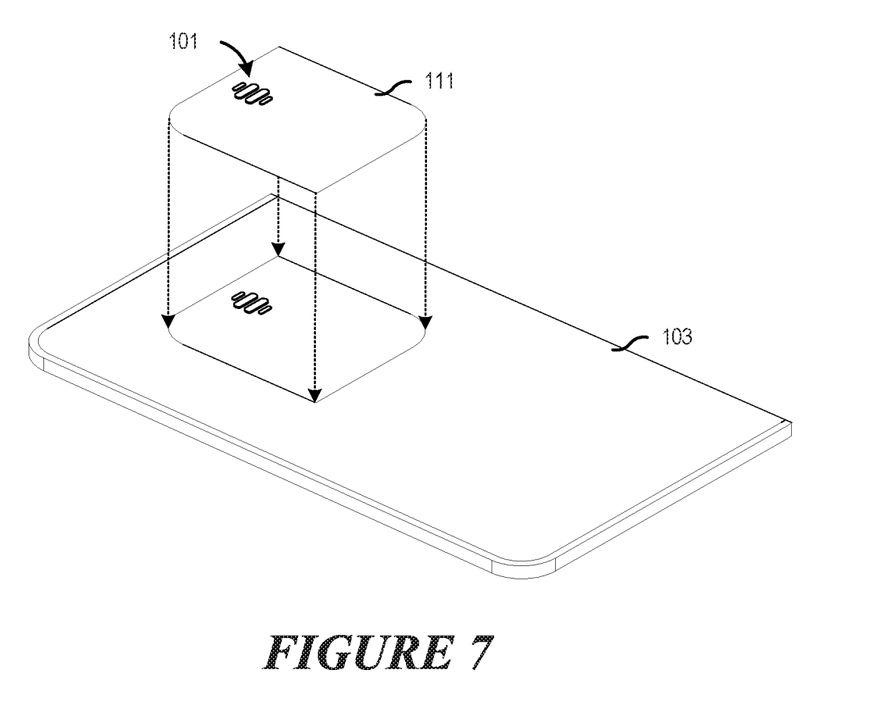
FIG. 7 is an embodiment NFC powered sensor having a sensor package in the form of a sticker positioned on a mobile device.
Figure 8:
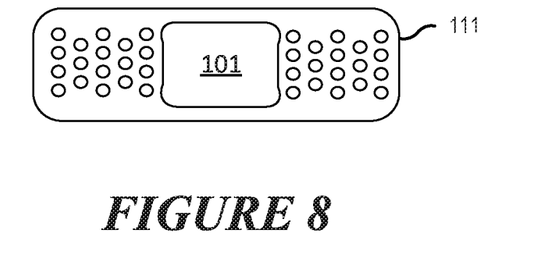
FIG. 8 is an embodiment NFC powered sensor having a sensor package in the form of an adhesive bandage.

A diagram of an embodiment network for communicating power and data is described using FIG. 1. In FIG. 2, a block diagram of an embodiment NFC powered sensor is described. A block diagram of an embodiment sensor module is described in FIG. 3. In FIG. 4, a block diagram of another embodiment sensor module is described. A block diagram of an embodiment NFC power receiver is described in FIG. 5. In FIG. 6, a block diagram of an embodiment NFC data transceiver is described. An embodiment NFC powered sensor having a sensor package in the form of a sticker positioned on a mobile device is described in FIG. 7. In FIG. 8, an embodiment NFC powered sensor having a sensor package in the form of an adhesive bandage is described. A block diagram of an embodiment NFC powered sensor with additional components is described in FIG. 9. In FIG. 10, an embodiment NFC powered sensor having a sensor package in the form of a sticker positioned on a mobile device and having an activation switch is described. A block diagram of an embodiment NFC powered sensor is described in FIG. 11. In the following discussion, the same elements are designated with the same reference numbers in the various figures.

FIG. 1 is a diagram of a network 100 for communicating power and data. The network 100 includes an NFC powered sensor 101, a mobile device 103, and, optionally, a remote server 105. As shown, the NFC powered sensor 101 establishes power (dashed line) and data (dotted line) connections with the mobile device 103, which respectively serve to power the NFC powered sensor 101 and carry data from the NFC powered sensor 101 to the mobile device 103 and vice-versa.

In some embodiments, a remote server 105 is provided that enables data communication between the remote server 105 and the mobile device 103. As an example, the mobile device 103 may communicate with the remote server 105 to transmit data collected by the NFC powered sensor 101. In another example, the mobile device 103 may receive calibration information (e.g., coefficients, look-up table, linear or non-linear equations, etc.) or information, relating to the specific NFC powered sensor 101, stored at the remote server 105.

In these embodiments, the mobile device 103 is an NFC capable device. The mobile device 103 may provide power to the NFC powered sensor 101 using electromagnetic induction, as established under the NFC communication standard protocols. Power is provided to the NFC powered sensor 101, which collects and measures a stimulus. The mobile device 103 receives, or reads, data from the NFC powered sensor 101. In some embodiments, the mobile device 103 analyzes the measured data or transmits the data to the remote server 105. The remote server 105 may independently of, or in combination with, the mobile device 103 analyze the received data from the NFC powered sensor 101 to determine, for example, trends in measurements, such as determining an increase or a decrease in environmental temperature over time.

Generally, during device manufacturing or design and prior to device delivery, sensors are characterized or calibrated in a controlled environment using calibrated equipment against a known or a standard stimulus input. A characterization curve is generated that may be used to map the level of a sensor measurement to a calibrated input. In some instances, each individual sensor is calibrated and a calibration correction in the form of, for example, a table, an equation, etc. is associated with the sensor. The calibration correction is used to provide a more accurate representation of the sensor measurement in the field.

In some embodiments, the NFC powered sensor 101 may transmit the raw data, without processing, to the mobile device 103. The mobile device 103 or the remote server 105, independently or in combination, may then use the calibration information to process and analyze the raw data. In some embodiments, the calibration information may be stored in a memory as a result of an installation of an application on the mobile device 103.

In some embodiments, the calibration information may be stored in a memory of the NFC powered sensor 101 and may be communicated to the mobile device 103. In some embodiments, the calibration information, as previously stated, may be stored at the remote server 105. The remote server 105 may receive the raw data and use the calibration information to analyze the data. Alternatively, the remote sever 105 may communicate the calibration information to the mobile device 103, for processing of the data.

In one embodiment, the NFC powered sensor 101 may transmit processed data to the mobile device. The processed data may then be further analyzed, for example, over time to determine trends in the processed and collected data. The NFC powered sensor 101 may receive calibration data for processing from the mobile device 103 or from an internal memory. The mobile device 103 and the remote server 105, independently or in combination, may further analyze the measurements.

In some embodiments, the NFC powered sensor 101 collects measurements in an internal memory when powered by the mobile device 103 using NFC technology without transmitting the data to the mobile device 103. Afterwards and in response to a trigger event, such as a request by the mobile device 103 or by exceeding a certain storage capacity of the memory, the NFC powered sensor 101 may transmit the collected information stored in memory to the mobile device 103.

FIG. 2 illustrates a block diagram of an embodiment NFC powered sensor 101 for performing methods described herein, which may be contained in a sensor package in external to the mobile device 103. The NFC powered sensor 101 includes a sensor module 113 having a detector 117 and a sensor circuit 119. The NFC powered sensor 101 may also comprise a NFC circuit 115 having an NFC power receiver 121 and an NFC data transceiver 123.

The detector 117 converts a physical, gas, or chemical stimulus to an electronic signal. In some embodiments, for example, in the case of a biosensor, the sensor circuit 117 may comprise a physiochemical detector. The physiochemical detector interacts with a biological or chemical analyte (i.e., a substance to be analyzed). A detector element (i.e., a transducer) transforms the biological or chemical signal to an electric signal, for example, a voltage or a current.

As another example of a detector 117, a gas sensor or gas detector may have a porous membrane connected to an electrode. The sensor detects the generation of, or a variation in, a current in accordance with the amount of gas diffused within the porous membrane.

In some embodiments, the detector 117 may comprise one or more MEMS sensors. The MEMS sensor converts a physical stimulus, for example, using capacitive pressure sensors to measure vibration, pressure, or acceleration.

The detector 117 may be a polymer based sensor, a graphene based sensor, a MOX based sensor, or any other type of sensor that is particularly susceptible to aging, which can be in the form of a MEMS sensor, or any other form of sensor well known in the arts.

In a polymer based sensor, a change in material properties (e.g., dielectric, resistance, volume, capacitive, etc.) is attributable to environmental effects, particularly corresponding to the specific design properties of the polymer sensor.

As an example, in an embodiment used to sense and measure hydration, the detector 117 upon exposure to water, absorbs and diffuses water molecules. The absorption and diffusion results in dimensional changes and swelling in the polymer. The swelling can be measured using conductive particles homogeneously spread throughout the polymer. As the swelling increases the separation of the conductive particles, the bulk resistance measurement of the polymer may be used as an indicator or, when properly calibrated, a measurement of moisture.

In some embodiments, the detector 117 may be a combination of several polymer based sensors. As an example, the detector 117 may be a combination of a resistive change polymer, a swelling polymer, or a capacitive shift polymer. The inclusion of several types of polymer sensors, advantageously, in a detector 117 working in combination, improves data accuracy and reduces measurement errors, reduces errors as a result of calibration errors or variations in the calibration, reduces aging related errors as a result of exposure to the environment, and enhances sensitivity and selectivity to ionic or conductive compounds of interest or to dielectric elements of interest in comparison with a single type polymer sensor.

The sensor circuit 119 receives the electric signal from the detector 117 corresponding to the associated measurement performed by the detector 117. FIG. 3 illustrates a block diagram of an embodiment sensor module 113 including the detector 117 and the sensor circuit 119. The sensor circuit 119 may include a memory 131 storage device, a microprocessor 133, a communications interface circuit 135, a sensor interface signal control circuit 137, a security/calibration data circuit 139, a current source 141, and an analog-to-digital converter (ADC) 143.

The sensor interface signal control circuit 137 may be used in conjunction with the microprocessor 133 to enable the current source 141 to provide a current to the detector 117. In an embodiment, the detector 117 may be a resistive change polymer, where the resistance of the detector 117 varies in response to a stimuli. The current provided by the current source 141 flows through the detector 117 and a voltage across the resistor, in reference to a ground source 145, is converted from an analog signal to a digital signal using the ADC 143. When the resistance in the detector 117 changes, in response to a stimulus, the associated voltage at the ADC 143 also changes.

The measurement from the ADC 143 is received at the sensor interface signal control circuit 137 of the sensor circuit 119. The raw data collected from the detector 117 can be processed by the microprocessor 133 using, for example, calibration data stored in the security/calibration data circuit 139. The raw data or the processed data may then be stored in the memory 131 of the sensor circuit 119. Additionally, the memory 131 may also contain instructions for measuring, collecting, processing, and transferring data from the sensor circuit 119 to the NFC circuit 115. The sensor circuit 119 may then transmit the raw data or the processed data from the sensor module 113 to the NFC circuit 115 using the communications interface circuit 135.

FIG. 4 illustrates a block diagram of another embodiment sensor module 113 including multiple detectors 117 and the sensor circuit 119. In FIG. 4, in addition to the components previously described, with respect to FIG. 3, multiple detectors 117, a current multiplexer 147, and multiple switches 149 are also included in the sensor module 113. Although in FIG. 4 only three detectors 117 are shown, multiples of detectors 117 may be contemplated.

As illustrated, each detector 117 is connected to the current source 141 and the current multiplexer 147 using a switch 149. In this configuration, depending on the switch 149 configuration, multiple measurements may be collected at the same time. Each measurement may be converted to a digital signal using the ADC 143 of the sensor module 113. In some embodiments, the switch 149, current source 141, and the current multiplexer 147, may be configured, for example using the microprocessor 133, to collect a measurement from an individual detector 117, as an independent unit, or collectively as a group of detectors 117. The number of active switches 149 and consequently active detectors 117 may be advantageously selected to minimize the amount of current (i.e. minimize power requirements) necessitated to properly operate the group of active detectors 117.

Figure 5:
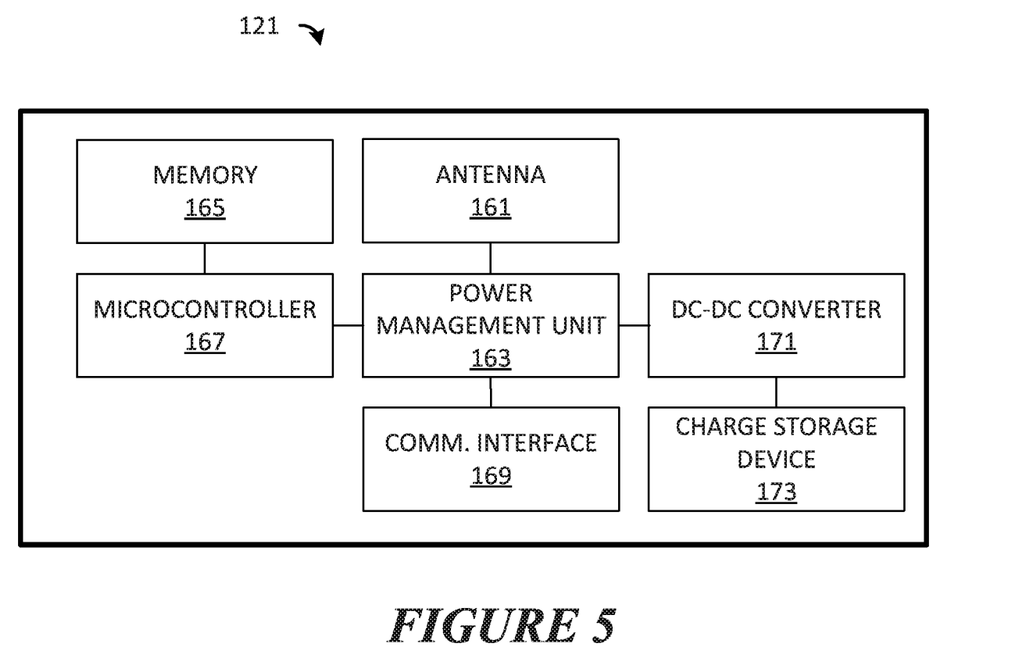
FIG. 5 illustrates a block diagram of an embodiment NFC power receiver.

FIG. 5 illustrates a block diagram of an embodiment NFC power receiver 121. As illustrated, the NFC power receiver 121 may include a receiving antenna 161 designed to operate at 13.56 megahertz (MHz) frequency, a power management unit 163, a memory 165 storage device, a microcontroller 167, a communication interface 169, a DC to DC converter 171, and a charge storage device 173.

The NFC power receiver 121 is a wireless circuit that receives inductive power provided by the mobile device 103, using NFC protocol standards, operating within the radio frequency band of 13.56 MHz In a typical NFC power receiver 121 the receiving antenna 161, for example a coil, acts as an inductor and the interacting magnetic field between the mobile device 103 and the NFC powered sensor 101 induces an electric current in the NFC power receiver 121. The receive antenna 161 may optionally have tuning circuitry for optimizing the performance of the receive antenna 161.

In some embodiments, the electric current is managed using the DC to DC converter 171 and the power management unit 163, and as a result, the induced electric current is adjusted to FIG. 5 illustrates a block diagram of an embodiment NFC power receiver a level suitable for the operation of the NFC powered sensor 101. In some embodiments, the NFC power receiver 121 may also include the memory 165 that stores instructions, which are processed by the microcontroller 167 to operate the NFC power receiver 121. In an embodiment, the NFC power receiver 121 may optionally include a charge storage device 173, such as capacitors, inductors, and battery units for charge storage.

The power induced at the NFC power receiver 121 is transferred to the various components of the NFC powered sensor 101 using the communication interface 169.

FIG. 6 illustrates a block diagram of an embodiment NFC data transceiver 123. The NFC data transceiver 123 includes a receive antenna 181, a transmit antenna 183, a microcontroller 185, a memory 187, a communication interface 189, and a data controller 191.

The NFC data transceiver 123 is a wireless circuit that receives and transmits data, respectively, from and to the mobile device 103. The NFC data transceiver 123 may have a separate transmit antenna 183 and a receive antenna 181 in the form of, for example, a coil. However, in some embodiments, the receive antenna 181 and the transmit antenna 183 may be a single antenna. In some embodiments, the NFC power receiver 121 and the NFC data transceiver 123 may have a single shared antenna, contributing to a more compact and thinner NFC powered sensor 101.

The NFC data transceiver 123 may also a data controller 191 used for framing and synchronizing tasks related to the data communication. The NFC data transceiver 123 has sensor and data inputs and outputs in the form of the communication interface 189 used to receive sensor information from the sensor module 113 and to transmit the sensor information to the mobile device 103.

The memory 187 may be configured to store instructions for the processing of the microcontroller 185 for proper operation of the NFC data transceiver 123.

As illustrated, the detector 117 and the sensor circuit 119 are separate components of the NFC powered sensor 101, however, a device having functionalities of both components may also be contemplated. Similarly, a single device having the functionalities of the NFC power receiver 121 and the NFC data transceiver 123 may also be contemplated.

Referring back to FIG. 2, the sensor package in houses the sensor module 113 and the NFC circuit 115. The sensor package may be selected, from an assortment of form factors, in accordance with the stimuli to be measured.

In an embodiment, the sensor package 111 may be an external case that houses the mobile device 103. Alternatively, the sensor package 111 may be in the form of a sticker positioned on the mobile device 103 or positioned on a protective case of the mobile device 103, as illustrated in FIG. 7. In such an embodiment, the vicinity of the NFC powered sensor 101 to the mobile device 103 provides the possibility of near continuous operational capability.

As another example, the sticker may be in the form of an adhesive bandage (e.g., Band-Aid) covering a scab or a wound, as illustrated in FIG. 8. An embedded sensor in the sticker may detect the presence of dirt, bacteria, or infection at the wound or be quantified in levels as parts per million (PPM) in relation to, for example, blood contents. The adhesive bandage may also be used as a skin patch in a transdermal sensor to detect for example alcohol or ethanol content levels by measuring transdermal alcohol concentration at the skin surface.

In some embodiments, the sensor package 111 may be an implantable sensor used, for example, as a health sensor to measure blood flow, blood contents, body temperature, blood lead level, etc. The sensor package 111 may be designed to be inserted under the skin of a patient. The resulting implanted NFC powered sensor 101 can then measure and transmit data to an external mobile device 103 when the mobile device is positioned in vicinity of the NFC powered sensor 101.

In one embodiment, an article, which an individual has easy and constant access to, may be used as the sensor package 111. As an example, the sensor package 111 may be an article of clothing, a piece of jewelry (e.g., ring, necklace, etc.), a keychain, a device connected to a keychain, or a wallet.

In yet another embodiment, the sensor package 111 may be in the form of a medical or commercial sensing device. As an example, a swab used to take samples from an individual's saliva or forehead, a tongue depressor, or a thermometer may be used as the sensor package 111.

In summary, any device accessible with a mobile device 103 may be used as a sensor package 111. The NFC powered sensor 101 as a separate module to the mobile device 103, provides numerous advantages in an efficient sensing device in the form of the NFC powered sensor 101 and a universal data analysis device in the form of the mobile device 103.

In some embodiments, the sensor package 111 may be optimized to maximize the flow of air or liquid using back plates and MEMS structures in a variety of optimal chemical flow design techniques and patterns.

Figure 9:
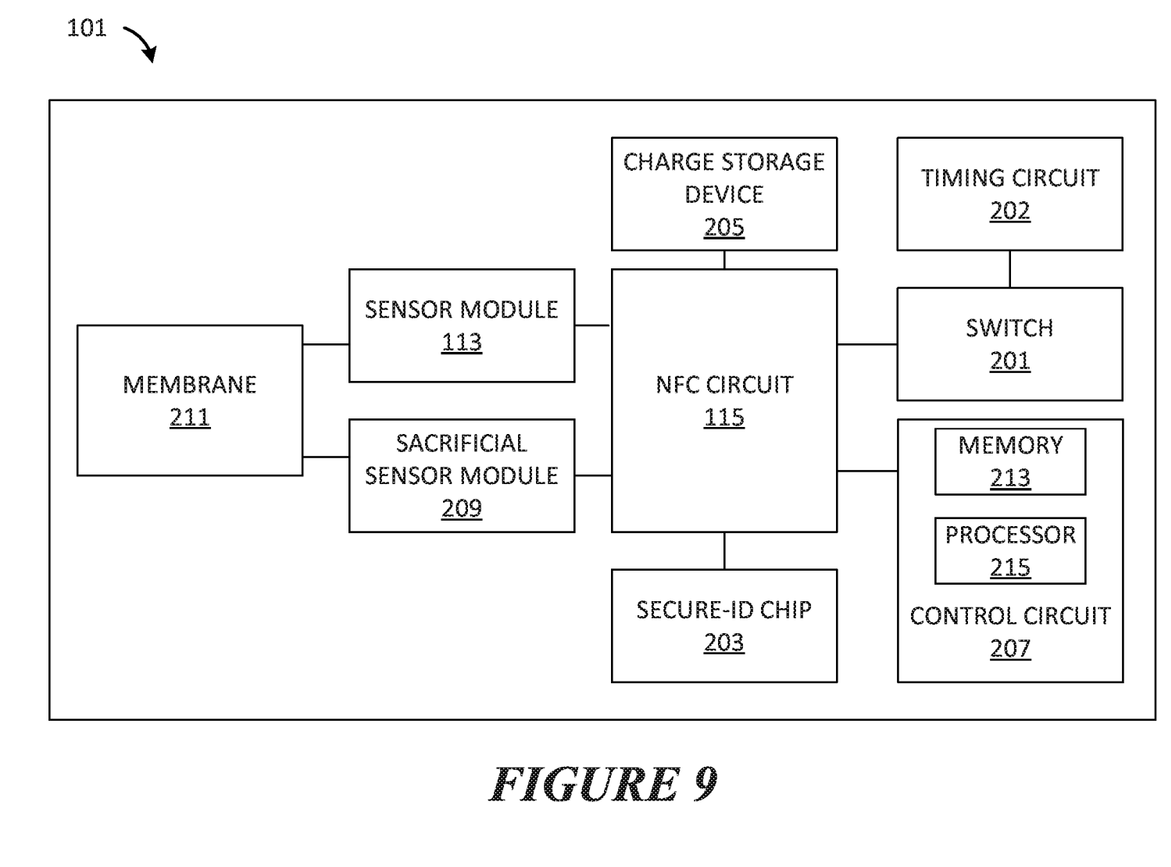
FIG. 9 is a block diagram of an embodiment NFC powered sensor with additional components.
Figure 10:
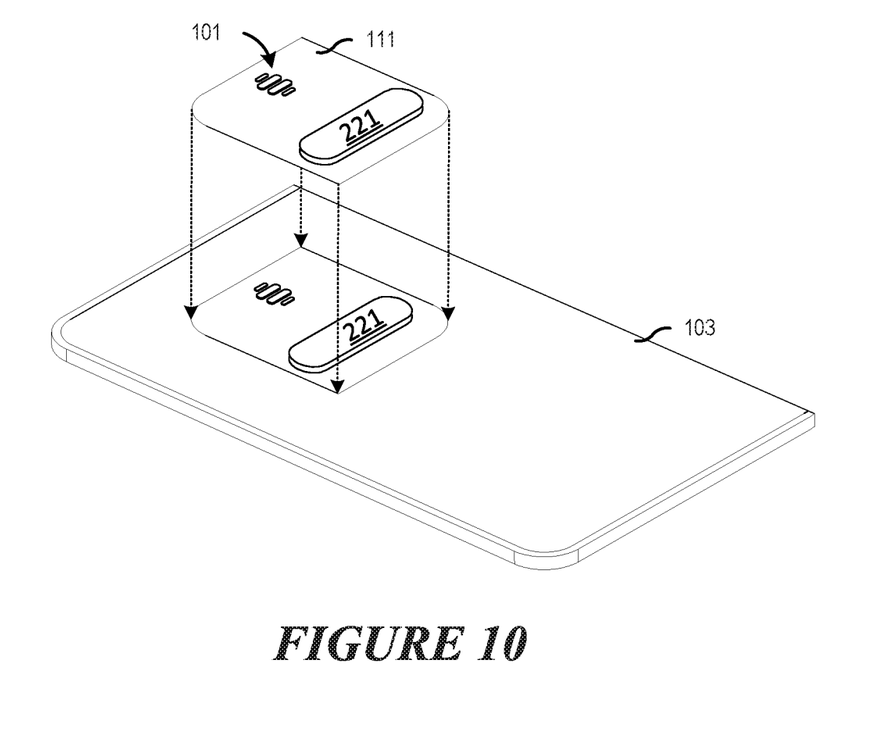
FIG. 10 is an embodiment NFC powered sensor having a sensor package in the form of a sticker positioned on a mobile device and having an activation switch.

FIG. 9 illustrates a block diagram of an embodiment NFC powered sensor 101 for performing methods described herein, which may be contained in the sensor package 111 external to the mobile device 103. As illustrated, the NFC powered sensor 101 in addition to the sensor module 113 and the NFC circuit 115, previously described above with respect to FIGS. 2-6, may optionally include a switch 201, a secure-id chip 203, a charge storage device 205, a control circuit 207, a sacrificial sensor module 209, and a membrane 211.

The switch 201 may be used to activate the process of sensing by the NFC powered sensor 101, which is typically in an inactive or in an unpowered state. The switch 201 helps assure that the device is turned on when desired and inhibits inadvertent NFC based triggering. As an example, the NFC powered sensor 101, to reduce interference with other operations of the mobile device 103, is in an inactive state when the mobile device 103 is being used, for example, in a payment transaction.

The switch 201 may be advantageous when the NFC powered sensor 101 is continuously positioned at the vicinity of the mobile device 103, for example, in the case of a sticker attached to the back of the mobile device 103. To reduce power draw by the sticker from the NFC powered sensor 101, and to improve power efficiency, the NFC powered sensor 101 is activated through the switch 201.

In an embodiment, the switch 201 may be a user action trigger switch (e.g., pushbutton switch, breath activated switch, application, etc.) that is externally triggered and used to activate the NFC powered sensor 101 when a measurement is to be taken and received by the mobile device 103.

As an example, the switch 201 may be activated in response to a user pressing down on a circuit component that closes a typically open circuit to activate the NFC powered sensor 101.

In another example, the switch 201 may be activated in response to a signal transmitted to the sensor module 113 by the mobile device 103 using an application on the mobile device 103. The application used to activate the NFC powered sensor 101 may be the same application used to communicate and receive measurements from the NFC powered sensor 101. The application may optionally request a user to activate the switch 201 by pressing down or depressing a designated pad 221 on the NFC powered sensor 101 as illustrated in FIG. 10.

In some embodiments, the switch 201 may be an internally triggered switch (e.g., timer, internal charge depletion, etc.) that activates the NFC powered sensor 101 in response to an internal event. In another example, the NFC powered sensor 101 may have a charge storage device 205 (e.g., capacitor, battery, etc.) that retains charge for a duration of time and is recharged using the NFC protocol by the mobile device 103. The NFC powered sensor 101 may be activated and taking measurements during a full charge mode or a charge depletion period related to the charge storage device 205 and deactivated during the recharging of the charge storage device 205.

As another example, the NFC powered sensor 101 may have an internal clock or timing circuit 202 that is used to take quantized measurements of the stimuli over a time period. The NFC powered sensor 101 may be activated, for example, every 5 minutes to take a measurement. At the completion of the measurement, the sensor may be deactivated until the next activation period. The internal clock or timing circuit may be part of the control circuit 207. The control circuit 207 in conjunction with the switch 201 may be used to activate the NFC powered sensor at set intervals.

As another example, the switch 201 may be activated in response to a patient breathing on the NFC powered sensor 101. The switch 201 may be activated in response to a contact formed from the condensation formed from the act of breathing. An accompanying circuit in the control circuit 207 may be continuously enabled, or alternatively and for power efficiency purposes be turned on at specific intervals, to detect a trigger such as the act of breathing by a subject. If the accompanying circuit in the control circuit 207 detects the trigger, the switch 201 may then be activated to detect the levels of bacteria in the air molecules exposed to the NFC powered sensor 101.

An additional benefit of the switch 201 is to reduce the tuning design requirements and potential damage caused by a secondary or non-compliant radio frequency (RF) radiating equipment at the receiving and transmitting antennas of the mobile device 103, the NFC powered sensor 101, and any other third-party NFC device.

Typically, multiple resonant circuits in the vicinity of each other result in an influence in the resonant circuit and a load change at the respective transmitting component. The detuning can result in reduced power efficiency, standard incompliance, and in some situations a damaged component.

The secure-id chip 203 may be used to provide an encrypted, secure identification, or two-factor authentication (2FA) of the NFC powered sensor 101 by the mobile device 103. As an example, during manufacturing, the device manufacturer may perform an individual characterization or calibration of each NFC powered sensor 101 or a calibration of a group (e.g., manufacturing lot, etc.) of NFC powered sensors 101.

In some embodiments, the calibration information, sensor specific data processing instructions (e.g., processing coefficients, processing equations, etc.), and/or sensor specific manufacturing details (e.g., date of manufacturing, operating life, etc.) may be stored in the remote server 105 and tagged with an identification number (e.g., encrypted serial number) associated with the NFC powered sensor 101 or the manufacturing lot of the NFC powered sensor 101. The mobile device 103 may use the secure identification information provided by the secure-id chip 203 to communicate with the remote server 105 to receive the corresponding information, for example, the calibration information specific to the NFC powered sensor 101. This allows a secure and individualized calibrated analysis to be performed by the mobile device 103 or the remote server 105.

In another embodiment, the calibration information, sensor specific data processing instructions, and/or sensor specific manufacturing details may be stored in the secure-id chip 203. The secure-id chip 203 may have a storage component of a non-volatile memory type that stores this information, which can be securely accessed by the mobile device using NFC technology.

The secure-id chip 203 may also be used as a device certification instrument to prevent unauthorized access to the electronic data stored on the NFC powered sensor 101 or to prevent the use of unauthorized versions (e.g., illegal counterfeits or knockoffs) of the NFC powered sensor 101. The secure-id chip 203 may also be used as an access authorization utility to provide the mobile device 103 or the NFC powered sensor 101 with additional information not available during product manufacturing. As an example, the mobile device 103 may be able to access lot information pertaining to a product recall or an adjustment to the processing instructions from the remote server 105 using the secure-id chip 203 information of the NFC powered sensor 101.

The sacrificial sensor module 209 may have the same components as, and function similarly to, the sensor module 113. However, unlike the sensor module 113, the sacrificial sensor module 209 is not exposed and is isolated from the stimuli. As an example, the sacrificial sensor module 209 may be completely isolated or may only be exposed to a limited set of stimuli.

During the operating life of the NFC powered sensor 101, the NFC powered sensor 101 is exposed to various environmental events (e.g., temperature cycles, etc.), which can potentially cause a variation and drift in the values of the measurements over the operating life of the NFC powered sensor 101. As the sacrificial sensor module 209 is exposed to similar environmental exposures as the sensor module 113, variations and drifts in the measurements caused by an exposure to heat, cold, shock, humidity, or assembly is shared between the sacrificial sensor module 209 and the sensor module 113. The measurements from the sacrificial sensor module 209 may then be used as a baseline measurement or a calibration reference to exclude changes due to polymer shifts from environmental (e.g., temperature, gases) aging and improve measurement accuracy through corresponding correction factors.

The sacrificial sensor module 209 may also be used to indicate the NFC powered sensor 101 end of life and disposal time. The data output from the sacrificial sensor module 209 may be compared against a threshold of acceptability, which if not satisfied, may indicate the end of life of the NFC powered sensor 101.

In some embodiments, the sacrificial sensor module 209 may be located on an opposite of the sensor module 113, which is not exposed to the stimuli. In some embodiments, the sacrificial sensor module 209 may comprise a membrane filter that isolates the sacrificial sensor module 209 from exposure to the specific stimuli exposed to the sensor module 113.

The control circuit 207 may be used to process the raw data collected by the sensor module 113 and the sacrificial sensor module 209. The control circuit 207 may include a memory 213 and a processor 215 for executing instructions stored in the memory 213. In some embodiments, the processor 215 may be used to process instructions to collect sensor information and transmit the information to the mobile device 103 using the NFC circuit 115. In some embodiments, the control circuit 207 may be used to control the various components of the NFC powered sensor 101. The memory 213 may also be used to store measurements collected from the sensor module 113 and/or the sacrificial sensor module 209.

The memory 213 may also be used to store sensor calibration information and/or processor-executable instructions to be processed by the processor of the control circuit 207. The memory 213 may be implemented as a non-transitory processor-readable medium (e.g., electrically erasable programmable read-only memory (EEPROM), etc.) that receives power through the NFC power receiver 121, the charge storage device 205, an optional capacitor or an optional battery in the NFC circuit 115. The non-transitory medium could include one or more solid-state memory devices and/or memory devices with movable and possibly removable storage media.

The membrane 211 may act as a filter of sorts to effectively permit only the particles or particulates to be received by the sensor module 113. In some embodiments, multiple membranes may be used to filter inputs for different types of sensors of the NFC powered sensor 101. As an example, a fluid block membrane may be used on a breath sensor to detect certain properties of the air molecules, while an organic block membrane may be used on a liquid sensor to detect specific details of the water molecules.

As another example, a type of membrane filter, such as a Gore-Tex material, may be used to block water but allow air to reach the NFC powered sensor 101. In another example, a type of membrane filter, such as simple plastic, allows pressure and temperature stimuli to pass but prevents exposure to liquid at the NFC powered sensor 101. In yet another example, a hydrophobic material may be used to block exposure to water but allow alcohol or oil to pass through.

The membrane 211 may be part of the sensor package 111 or, alternatively, applied as a coating on the sensor module 113 (on-die membrane). The use of on-die membranes and multi-membrane packaging allows for a broader range of applications in smart nose devices (i.e. multi-sensor devices).

As an example, in a multi-sensor NFC powered sensor 101, such as that shown in FIG. 4, each detector 117 or a group of detectors 117 may be designed to measure different stimuli. In such a device, each detector 117 or group of detectors 117 may have a separate membrane filter 211 to isolate exposure to the particular stimuli associated with the configuration. One group of detectors 117 may have a membrane filter 211 that prevents exposure to liquids but allows exposure to air, while a second group of detectors 117 may have a membrane filter 211 that prevents exposure to air but allow exposure to liquids.

Figure 11:
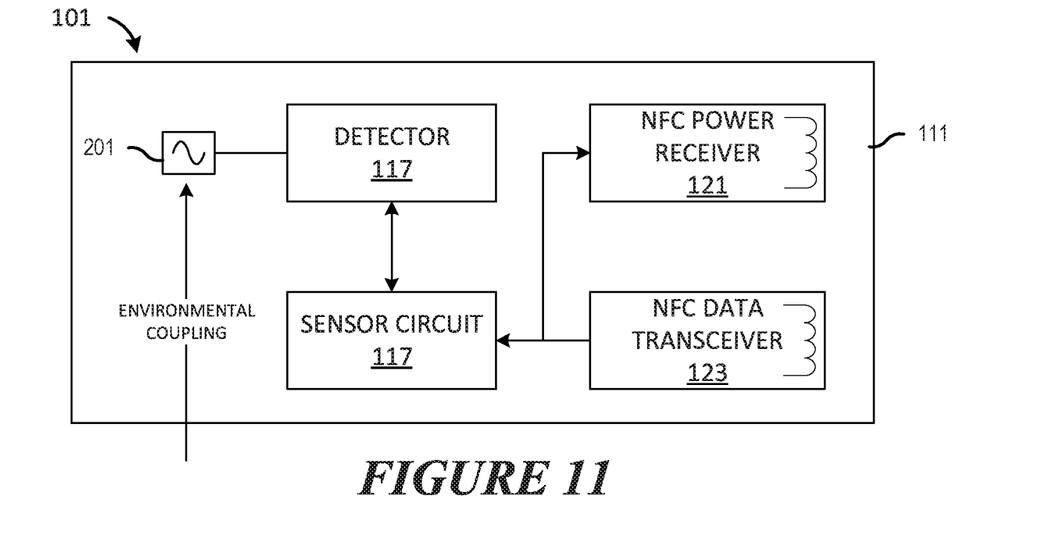
FIG. 11 is a block diagram of an embodiment NFC powered sensor.

FIG. 11 illustrates a schematic of an embodiment NFC powered sensor 101 for performing methods described herein. As illustrated, the NFC powered sensor 101 receives a physical or chemical stimulus, optionally, at an environmentally coupled filter 201.

The detector 117 senses the stimulus and the sensor circuit 117 sends the measurement to the mobile device 103 using the NFC data transceiver 123. The NFC powered sensor 101 is powered using the NFC power receiver 121.

Example embodiments of the present invention are summarized here. Other embodiments can also be understood from the entirety of the specification and the claims filed herein.

Example 1

A sensor device includes a first detector circuit, a near field communication (NFC) circuit, and a sensor package. The first detector circuit configured to detect a stimulus using a resistive change polymer type detector, a capacitive shift polymer type detector, a dielectric change polymer type detector, a graphene based sensor, or a metal-oxide (MOX) type detector. The NFC circuit having an NFC powered receiver and an NFC data transceiver. The NFC power receiver configured to receive power from a mobile device using an NFC standard protocol and to provide operating power for the sensor device. The NFC data transceiver configured to transmit data to the mobile device using the NFC standard protocol, the data corresponding to the first stimulus. The sensor package configured to house the first detector circuit and the NFC circuit.

Example 2

The sensor device of example 1, further including a first membrane filter configured to direct the first stimulus to the first detector circuit and block an undesired stimulus from the first detector circuit.

Example 3

The sensor device of example 1 or 2, further including a second detector circuit configured to detect a second stimulus, where the second detector circuit includes a resistive change polymer, a capacitive shift polymer, a dielectric change polymer, a graphene based sensor, or a metal-oxide (MOX) type detector.

Example 4

The sensor device of one of examples 1, 2, or 3, further including a second membrane filter configured to direct the second stimulus to the second detector circuit and block a second undesired stimulus from the second detector circuit.

Example 5

The sensor device of example 1, where the sensor package has a form factor of a sticker.

Example 6

The sensor device of example 1, where the sensor package has a form factor of an adhesive bandage.

Example 7

The sensor device of example 1, further including a sacrificial sensor circuit. The sacrificial sensor circuit including a second detector circuit configured to be isolated from the first stimulus using a membrane filter and the sacrificial sensor circuit configured as a reference measurement used to determine a drift in performance of the first detector circuit.

Example 8

The sensor device of example 1, further including a secure-id chip configured to provide a secure access to the sensor device.

Example 9

The sensor device of example 1, further including a secure-id chip and a processor. The secure-id chip configured to store a calibration information of the sensor device and the processor configured to generate the data transmitted by the NFC data transceiver in accordance with the first stimulus and the calibration information.

Example 10

The sensor device of example 1, further including a secure-id chip configured to provide a verification of an authenticity of the sensor device.

Example 11

The sensor device of example 1, further including a secure-id chip configured to provide a secure reference tag used to retrieve sensor device information from an external device specific to the sensor device.

Example 12

A method for sensing a stimulus using a sensor device includes receiving, by a near field communication (NFC) circuit of the sensor device, an induced current from a mobile device using an NFC standard protocol, the induced current being used to power the sensor device. The method further includes detecting, by a detector circuit of the sensor device, a stimulus. The detector circuit being a resistive change polymer, a capacitive shift polymer, a dielectric change polymer, a graphene based sensor, or a metal-oxide (MOX) type detector. The method also includes converting, by a sensor circuit of the sensor device, the stimulus to a digital signal and transmitting, by an NFC data transceiver of the sensor device, the digital signal to the mobile device using the NFC standard protocol.

Example 13

The method of example 12, further including detecting, by a second detector circuit of the sensor device, a second stimulus, where the second detector circuit includes a resistive change polymer, a capacitive shift polymer, a dielectric change polymer, a graphene based sensor, or a metal-oxide (MOX) type detector. The method further includes converting, by the sensor circuit, the second stimulus to a second digital signal and transmitting, by the NFC data transceiver, the second digital signal to the mobile device.

Example 14

The method of example 12, further including filtering, by a membrane filter of the sensor device, undesired stimulants from the detector circuit and directing the stimulus to the detector circuit.

Example 15

The method of example 12, further including receiving, by the NFC data transceiver, data from the mobile device, where the data is used to convert the stimulus to the digital signal.

Example 16

The method of example 15, where the data includes calibration data or processing instructions.

Example 17

The method of example 12, further including detecting, by a sacrificial sensor circuit of the sensor device, a baseline measurement used to determine a drift in performance of the detector circuit.

Example 18

The method of example 17, further including determining an obsolescence of the detector circuit in accordance with the baseline measurement of the sacrificial sensor circuit.

Example 19

The method of example 12, where the detecting the stimulus further includes measuring the stimulus at predetermined time intervals in accordance with an internal clock or timing circuit.

Example 20

The method of example 12, further including activating the sensor device prior to detecting the stimulus, the sensor device being in a deactivated mode prior to being activated.

Example 21

The method of example 20, where the activating the sensor includes an activation of the sensor device in response to exposure to breath condensation by a user of the sensor device.

Example 22

A sensor device includes a detector circuit, a near field communication (NFC) circuit, a sensor circuit, a non-transitory memory storage, and a processor. The detector circuit includes a resistive change polymer, a capacitive shift polymer, a dielectric change polymer, a graphene based sensor, or a metal-oxide (MOX) type detector. The NFC power receiver includes an antenna and a power management unit. The NFC circuit configured to receive an induced current from a mobile device using an NFC standard protocol, where the induced current is used to operate the sensor device. The non-transitory memory storage includes instructions and the processor is in communication with the non-transitory memory storage. The processor executes instructions to detect a stimulus using the detector circuit, convert the stimulus to a digital signal using the sensor circuit, and transmit the digital signal to the mobile device using the NFC standard protocol by the NFC data transceiver circuit.

Example 23

The sensor device of example 22, further including a user action trigger switch, where the processor executes instructions to enable the sensor device to detect the stimulus upon activation of the user action trigger switch and disable the sensor device upon deactivation of the user action trigger switch.

Example 24

The sensor device of example 23, where the activation of the user action trigger switch includes coupling the antenna of the NFC power receiver to the power management unit.

Example 25

The sensor device of example 23, where the deactivation of the user action trigger switch includes decoupling the antenna of the NFC power receiver from the power management unit.

Example 26

The sensor device of example 22, where the processor executes instructions to receive calibration data from the mobile device, where the stimulus is converted to the digital signal using the calibration data.

Example 27

The sensor device of example 22, where the processor executes instructions to store the digital signal in the non-transitory memory storage.

Example 28

The sensor device of example 22, where the sensor device is in a deactivated mode, and where the processor executes instructions to activate the sensor device in response to triggering a switch of the sensor device.

Example 29

The sensor device of example 28 further including a charge storage device configured to store a power charge in accordance with the induced current received by the NFC.

While this invention has been described with reference to illustrative embodiments, this description is not intended to be construed in a limiting sense. Various modifications and combinations of the illustrative embodiments, as well as other embodiments of the invention, will be apparent to persons skilled in the art upon reference to the description. It is therefore intended that the appended claims encompass any such modifications or embodiments.

What is claimed is:
1. A sensor device comprising:
a first detector circuit configured to detect a first stimulus;
a sacrificial sensor circuit comprising a sacrificial detector circuit, wherein the sacrificial detector circuit is configured to be isolated from the first stimulus using a membrane filter, and wherein the sacrificial sensor circuit is configured as a reference measurement to determine a drift in performance of the first detector circuit;
a near field communication (NFC) circuit comprising:
an NFC power receiver configured to receive power from a mobile device using an NFC standard protocol and to provide operating power for the sensor device; and
an NFC data transceiver configured to transmit data to the mobile device using the NFC standard protocol, the data corresponding to the first stimulus; and
a sensor package configured to house the first detector circuit and the NFC circuit.
2. The sensor device of claim 1, further comprising a first membrane filter configured to:
direct the first stimulus to the first detector circuit; and
block an undesired stimulus from the first detector circuit.
3. The sensor device of claim 2, further comprising a second detector circuit configured to detect a second stimulus, wherein the second detector circuit comprises a resistive change polymer, a capacitive shift polymer, a dielectric change polymer, a graphene based sensor, or a metal-oxide (MOX) type detector.
4. The sensor device of claim 3, further comprising a second membrane filter configured to:
direct the second stimulus to the second detector circuit; and
block a second undesired stimulus from the second detector circuit.
5. The sensor device of claim 1, wherein the sensor package has a form factor of a sticker.
6. The sensor device of claim 1, wherein the sensor package has a form factor of an adhesive bandage.
7. The sensor device of claim 1, further comprising a secure-id chip configured to provide a secure access to the sensor device.
8. The sensor device of claim 1, further comprising:
a secure-id chip configured to store a calibration information of the sensor device; and
a processor configured to generate the data transmitted by the NFC data transceiver in accordance with the first stimulus and the calibration information.
9. The sensor device of claim 1, further comprising a secure-id chip configured to provide a verification of an authenticity of the sensor device.
10. The sensor device of claim 1, further comprising a secure-id chip configured to provide a secure reference tag used to retrieve sensor device information from an external device specific to the sensor device.
11. A method of sensing a stimulus using a sensor device, the method comprising:
receiving, by a near field communication (NFC) circuit of the sensor device, an induced current from a mobile device using an NFC standard protocol, the induced current being used to power the sensor device;

detecting, by a first detector circuit of the sensor device, a first stimulus;

detecting, by a second detector circuit of the sensor device, a second stimulus;

converting, by a sensor circuit of the sensor device, the first stimulus and the second stimulus to a first digital signal and to a second digital signal, respectively; and transmitting, by an NFC data transceiver of the sensor device, the first digital signal and the second digital signal to the mobile device using the NFC standard protocol.

12. The method of claim 11, further comprising filtering, by a membrane filter of the sensor device, undesired stimulants from the first detector circuit and directing the stimulus to the first detector circuit.

13. The method of claim 11, further comprising receiving, by the NFC data transceiver, data from the mobile device, wherein the data is used to convert the stimulus to the first digital signal.

14. The method of claim 13, wherein the data comprises calibration data or processing instructions.

15. The method of claim 11, further comprising detecting, by a sacrificial sensor circuit of the sensor device, a baseline measurement used to determine a drift in performance of the first detector circuit.

16. The method of claim 15, further comprising determining an obsolescence of the first detector circuit in accordance with the baseline measurement of the sacrificial sensor circuit.

17. The method of claim 11, wherein the detecting the stimulus further comprises measuring the stimulus at predetermined time intervals in accordance with an internal clock or timing circuit.

18. The method of claim 11, further comprising activating the sensor device prior to detecting the stimulus, the sensor device being in a deactivated mode prior to being activated.

19. The method of claim 18, wherein the activating the sensor device comprises an activation of the sensor device in response to exposure to breath condensation by a user of the sensor device.

20. A sensor device comprising:
a detector circuit;
a near field communication (NFC) power receiver comprising an antenna and a power management unit, the NFC power receiver configured to receive an induced current from a mobile device using an NFC standard protocol, wherein the induced current is used to operate the sensor device;
a sensor circuit;
an NFC data transceiver circuit;
a non-transitory memory storage comprising instructions;
a processor in communication with the non-transitory memory storage, wherein the processor executes instructions to:
detect a stimulus using the detector circuit,
convert the stimulus to a digital signal using the sensor circuit, and
transmit the digital signal to the mobile device using the NFC standard protocol by the NFC data transceiver circuit; and
a user action trigger switch, wherein the processor executes instructions to:
enable the sensor device to detect the stimulus upon activation of the user action trigger switch, and
disable the sensor device upon deactivation of the user action trigger switch.

21. The sensor device of claim 20, wherein the activation of the user action trigger switch comprises coupling the antenna of the NFC power receiver to the power management unit.

22. The sensor device of claim 20, wherein the deactivation of the user action trigger switch comprises decoupling the antenna of the NFC power receiver from the power management unit.

23. The sensor device of claim 20, wherein the processor executes instructions to receive calibration data from the mobile device, wherein the stimulus is converted to the digital signal using the calibration data.

24. The sensor device of claim 20, wherein the processor executes instructions to store the digital signal in the non-transitory memory storage.

25. The sensor device of claim 20, wherein the sensor device is in a deactivated mode, and wherein the processor executes instructions to activate the sensor device in response to triggering a switch of the sensor device.

26. The sensor device of claim 25 further comprising a charge storage device configured to store a power charge in accordance with the induced current received by the NFC.

27. The sensor device of claim 1, wherein the first detector circuit comprises a resistive change polymer, a capacitive shift polymer, a dielectric change polymer, a graphene based sensor, or a metal-oxide (MOX) type detector.

28. The method of claim 11, wherein each of the first detector circuit and the second detector circuit comprises a resistive change polymer, a capacitive shift polymer, a dielectric change polymer, a graphene based sensor, or a metal-oxide (MOX) type detector.

29. The sensor device of claim 20, wherein the detector circuit comprises a resistive change polymer, a capacitive shift polymer, a dielectric change polymer, a graphene based sensor, or a metal-oxide (MOX) type detector.

* * * * *